(12) United States Patent
Karg

(10) Patent No.: US 10,695,109 B2
(45) Date of Patent: Jun. 30, 2020

(54) INTRAMEDULLARY NAIL WITH CANNULATION ACCESS HOLE

(71) Applicant: DEPUY SYNTHES PRODUCTS, INC., Raynham, MA (US)

(72) Inventor: Nicholas Karg, Solothurn (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/840,389

(22) Filed: Dec. 13, 2017

(65) Prior Publication Data

US 2019/0175232 A1    Jun. 13, 2019

(51) Int. Cl.
| | |
|---|---|
| *A61B 17/72* | (2006.01) |
| *A61B 17/74* | (2006.01) |
| *A61B 17/17* | (2006.01) |
| *A61B 17/92* | (2006.01) |

(Continued)

(52) U.S. Cl.
CPC ...... *A61B 17/7233* (2013.01); *A61B 17/1707* (2013.01); *A61B 17/1725* (2013.01); *A61B 17/72* (2013.01); *A61B 17/7283* (2013.01); *A61B 17/744* (2013.01); *A61B 17/1717* (2013.01); *A61B 17/864* (2013.01); *A61B 17/921* (2013.01); *A61B 2017/561* (2013.01)

(58) Field of Classification Search
CPC ............ A61B 17/7233; A61B 17/7283; A61B 17/744; A61B 17/1717; A61B 17/864; A61B 17/921
USPC .................................. 606/62–64, 92–94, 102
See application file for complete search history.

(56) References Cited

U.S. PATENT DOCUMENTS 4,781,181 A  *  11/1988  Tanguy ................ A61B 17/164
                                                    606/64
4,877,019 A  *  10/1989  Vives ................. A61B 17/1707
                                                    606/64

(Continued)

FOREIGN PATENT DOCUMENTS

| EP | 0441577 A2 | 8/1991 |
| EP | 1510174 A1 | 3/2005 |

(Continued)

OTHER PUBLICATIONS

Smith & Nephew, Trigen Sureshot, Distal Targeting System V2.1, User Manual, 2011, 38 pages.

*Primary Examiner* — Pedro Philogene
*Assistant Examiner* — David C Comstock
(74) *Attorney, Agent, or Firm* — BakerHostetler

(57) ABSTRACT

In one embodiment, an intramedullary nail has a nail body that has a proximal end and a distal end that are offset from one another such that the body is elongate from the proximal end to the distal end. The body has an outer surface, and an inner surface. The inner surface defines a cannulation that extends into the proximal end towards the distal end. The body defines a proximal bone-anchor hole that extends into the outer surface and entirely through the nail, and a distal bone-anchor hole that extends into the outer surface and entirely through the intramedullary nail at a location between the proximal bone-anchor hole and the distal end. The nail also defines an access hole extends into the outer surface between the leading portion and the trailing portion. The access hole terminates at the cannulation and is in communication with the cannulation.

20 Claims, 8 Drawing Sheets

(51) Int. Cl.
*A61B 17/86* (2006.01)
*A61B 17/56* (2006.01)

(56) References Cited

U.S. PATENT DOCUMENTS

| | | | |
|---|---|---|---|
| 5,514,137 A * | 5/1996 | Coutts | A61B 17/7098 606/62 |
| 6,183,477 B1 | 2/2001 | Pepper | |
| 6,201,387 B1 | 3/2001 | Govari | |
| 6,223,066 B1 | 4/2001 | Govari | |
| 6,498,944 B1 | 12/2002 | Ben-Haim et al. | |
| 6,565,573 B1 | 5/2003 | Ferrante et al. | |
| 6,636,769 B2 | 10/2003 | Govari et al. | |
| 6,638,231 B2 | 10/2003 | Govari et al. | |
| 6,648,889 B2 | 11/2003 | Bramlet et al. | |
| 6,652,464 B2 | 11/2003 | Schwartz et al. | |
| 6,658,300 B2 | 12/2003 | Govari et al. | |
| 6,746,404 B2 | 6/2004 | Schwartz | |
| 6,783,499 B2 | 8/2004 | Schwartz | |
| 6,992,477 B2 | 1/2006 | Govari | |
| 6,995,729 B2 | 2/2006 | Govari et al. | |
| 6,996,431 B2 | 2/2006 | Ben-Haim et al. | |
| 7,060,075 B2 | 6/2006 | Govari et al. | |
| 7,520,185 B2 | 4/2009 | Baldewein et al. | |
| 7,525,309 B2 | 4/2009 | Sherman et al. | |
| 7,734,327 B2 | 6/2010 | Colquhoun | |
| 7,814,916 B2 | 10/2010 | Revie et al. | |
| 7,816,915 B2 | 10/2010 | Susel et al. | |
| 7,885,701 B2 | 2/2011 | DiSilvestro et al. | |
| 7,894,872 B2 | 2/2011 | Sherman | |
| 8,068,648 B2 | 11/2011 | DiSilvestro et al. | |
| 8,623,023 B2 | 1/2014 | Ritchey et al. | |
| 8,689,801 B2 | 4/2014 | Ritchey et al. | |
| 8,739,801 B2 | 6/2014 | Rains et al. | |
| 9,192,399 B2 | 11/2015 | Ritchey et al. | |
| 9,539,037 B2 | 1/2017 | Janna et al. | |
| 9,820,760 B2 | 11/2017 | Purohit | |
| 2002/0107445 A1 | 8/2002 | Govari | |
| 2003/0018246 A1 | 1/2003 | Govari et al. | |
| 2003/0036695 A1 | 2/2003 | Govari | |
| 2003/0040670 A1 | 2/2003 | Govari | |
| 2003/0120150 A1 | 6/2003 | Govari | |
| 2004/0034355 A1 | 2/2004 | Govari et al. | |
| 2004/0068178 A1 | 4/2004 | Govari | |
| 2004/0102696 A1 | 5/2004 | Govari | |
| 2005/0245821 A1 | 11/2005 | Govari et al. | |
| 2007/0283773 A1 | 12/2007 | Baldewein et al. | |
| 2008/0294258 A1 | 11/2008 | Revie et al. | |
| 2009/0099445 A1 | 4/2009 | Burger | |
| 2009/0171197 A1 | 7/2009 | Burger et al. | |
| 2010/0179550 A1 * | 7/2010 | Schreiber | A61B 17/1725 606/62 |
| 2011/0063094 A1 | 3/2011 | Meiertoberens et al. | |
| 2011/0098577 A1 | 4/2011 | DiSilvestro et al. | |
| 2012/0029432 A1 | 2/2012 | Sweeney | |
| 2012/0239039 A1 * | 9/2012 | Nardini | A61B 17/1725 606/64 |
| 2015/0157370 A1 * | 6/2015 | Gross | A61B 17/72 604/506 |
| 2015/0305791 A1 | 12/2015 | Purohit | |
| 2018/0140311 A1 * | 5/2018 | Winshtein | A61B 17/1707 |

FOREIGN PATENT DOCUMENTS

| | | |
|---|---|---|
| EP | 1693011 A1 | 8/2006 |
| EP | 1836955 A1 | 9/2007 |
| EP | 1836957 A1 | 9/2007 |
| EP | 1836958 A1 | 9/2007 |
| EP | 2380514 A1 | 10/2011 |
| EP | 1803394 B1 | 1/2012 |
| WO | 2005/084544 A1 | 9/2005 |
| WO | 2005/087125 A2 | 9/2005 |
| WO | 2006/090134 A2 | 8/2006 |
| WO | 2006/090139 A1 | 8/2006 |
| WO | 2006/090141 A1 | 8/2006 |
| WO | 2006/129087 A1 | 12/2006 |
| WO | 2007125497 A1 | 11/2007 |

* cited by examiner

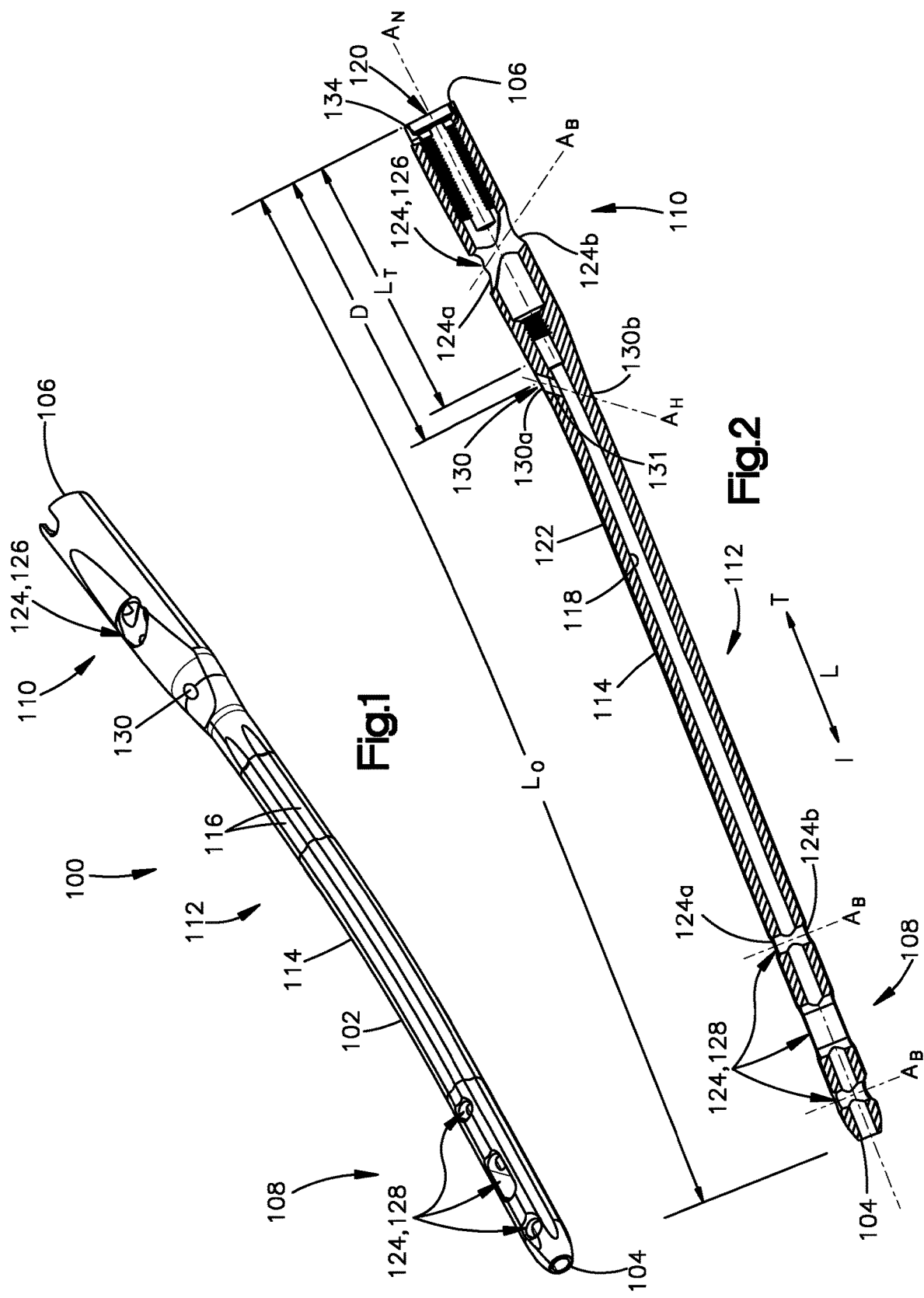

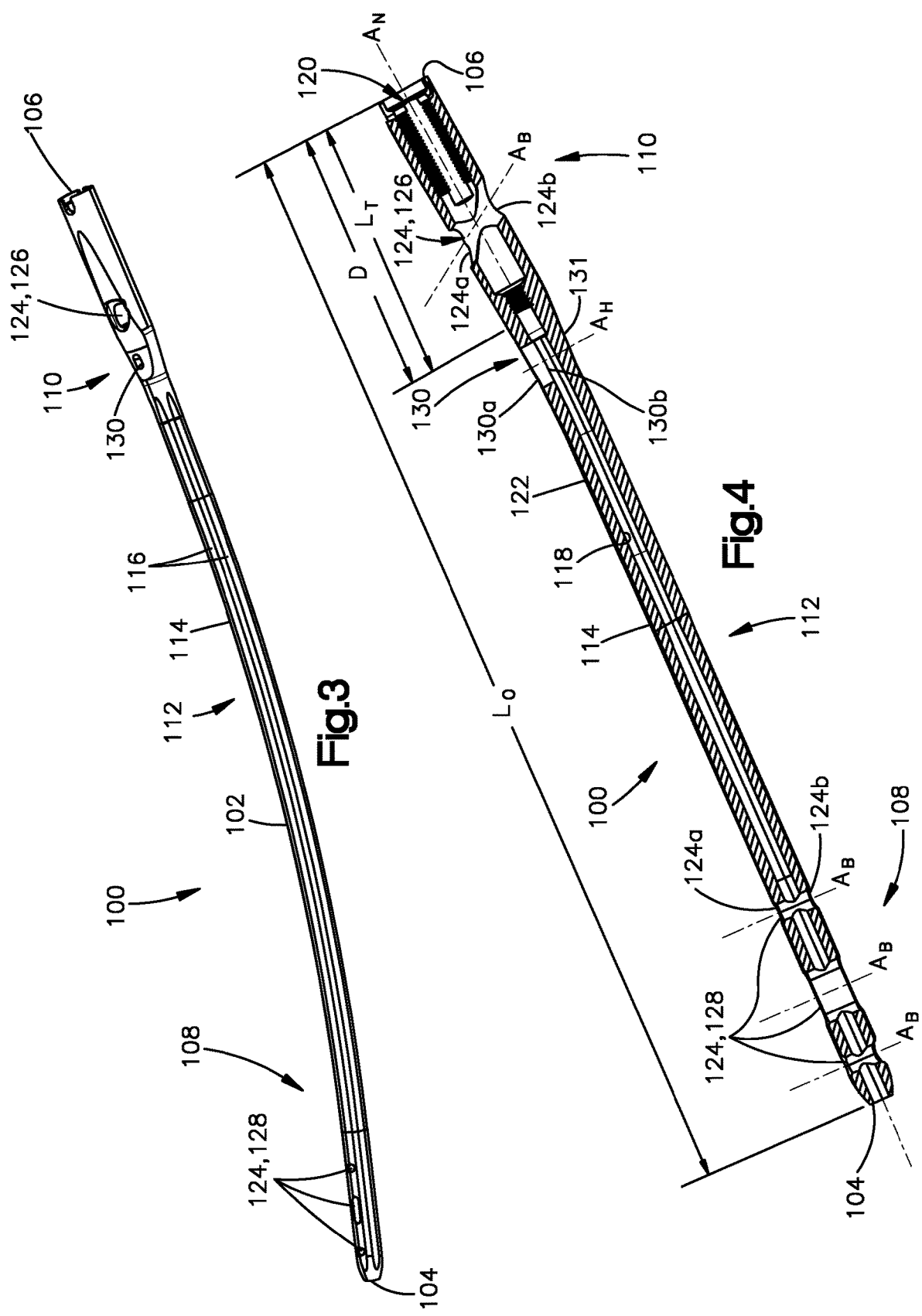

__US 10,695,109 B2__

INTRAMEDULLARY NAIL WITH CANNULATION ACCESS HOLE

TECHNICAL FIELD

The present disclosure relates to systems, assemblies, and methods for the insertion and fixation of a nail into an intramedullary canal of a bone.

BACKGROUND

Intramedullary nails are commonly used to treat fractures in long bones of the body such as fractures in femurs, tibias, and humeri. To treat such fractures, the intramedullary nail is inserted into a medullary canal of the long bone such that the nail spans across one or more fractures to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example embodiment, an intramedullary nail comprises a nail body having a proximal end and a distal end that are offset from one another such that the nail body is elongate from the proximal end to the distal end. The nail body has an outer surface that extends from the proximal end to the distal end, and that defines a perimeter of the intramedullary nail. The nail body has an inner surface that defines a cannulation that extends into the proximal end in a direction that extends toward the distal end. The nail body defines at least one proximal bone-anchor locking hole that extends into the outer surface and entirely through the intramedullary nail. The nail body defines at least one distal bone-anchor locking hole that extends into the outer surface and entirely through the intramedullary nail at a location between the at least one proximal bone-anchor locking hole and the distal end. The nail body defines an access hole that extends into the outer surface between the at least one proximal bone-anchor locking hole and the at least one distal bone-anchor locking hole. The access hole terminates as the cannulation and is in communication with the cannulation.

Another example embodiment includes a method of implanting an intramedullary nail into a bone. In the method, the intramedullary nail is inserted into a medullary canal of the bone such that the intramedullary nail is elongate along the medullary canal from a proximal end of the intramedullary nail to a distal end of the intramedullary nail. A probe is guided into a cannulation of the intramedullary nail through an access hole that extends into an outer surface of the intramedullary nail between a proximal bone-anchor locking hole and a distal bone-anchor locking hole. The probe is directed along the cannulation towards a select locking hole of the proximal and distal bone-anchor locking holes until a locator of the probe is proximate to the select locking hole. A location of the select locking hole is detected based on a position of the locator, and a cutting instrument is aligned with the select locking hole based on the detected location. A bore is formed in the bone with the cutting instrument such that the bore extends to the select locking hole. A bone anchor is inserted through the bore and into the select locking hole so as to secure the intramedullary nail to the bone.

Another example embodiment includes a method of promoting healing of a bone. In the method, an intramedullary nail is inserted into a medullary canal of the bone such that the intramedullary nail is elongate along the medullary canal from a proximal end of the intramedullary nail to a distal end of the intramedullary nail. A flowable substance is injected into a cannulation of the intramedullary nail through an access hole that extends into an outer surface of the intramedullary nail between a proximal bone-anchor locking hole and a distal bone-anchor locking hole. The flowable substance is discharged out of the cannulation and into the bone through at least one discharge hole that extends into the outer surface of the intramedullary nail between the proximal bone-anchor locking hole and the distal bone-anchor locking hole.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1 shows a perspective view of an intramedullary nail according to one embodiment having an access hole that provides access to a cannulation in the intramedullary nail;

FIG. 2 shows a cross-sectional side view of the intramedullary nail of FIG. 1;

FIG. 3 shows a perspective view of an intramedullary nail according to another embodiment having an access hole that provides access to a cannulation in the intramedullary nail;

FIG. 4 shows a cross-sectional side view of the intramedullary nail of FIG. 3;

DETAILED DESCRIPTION OF ILLUSTRATIVE EMBODIMENTS

Figure 5:
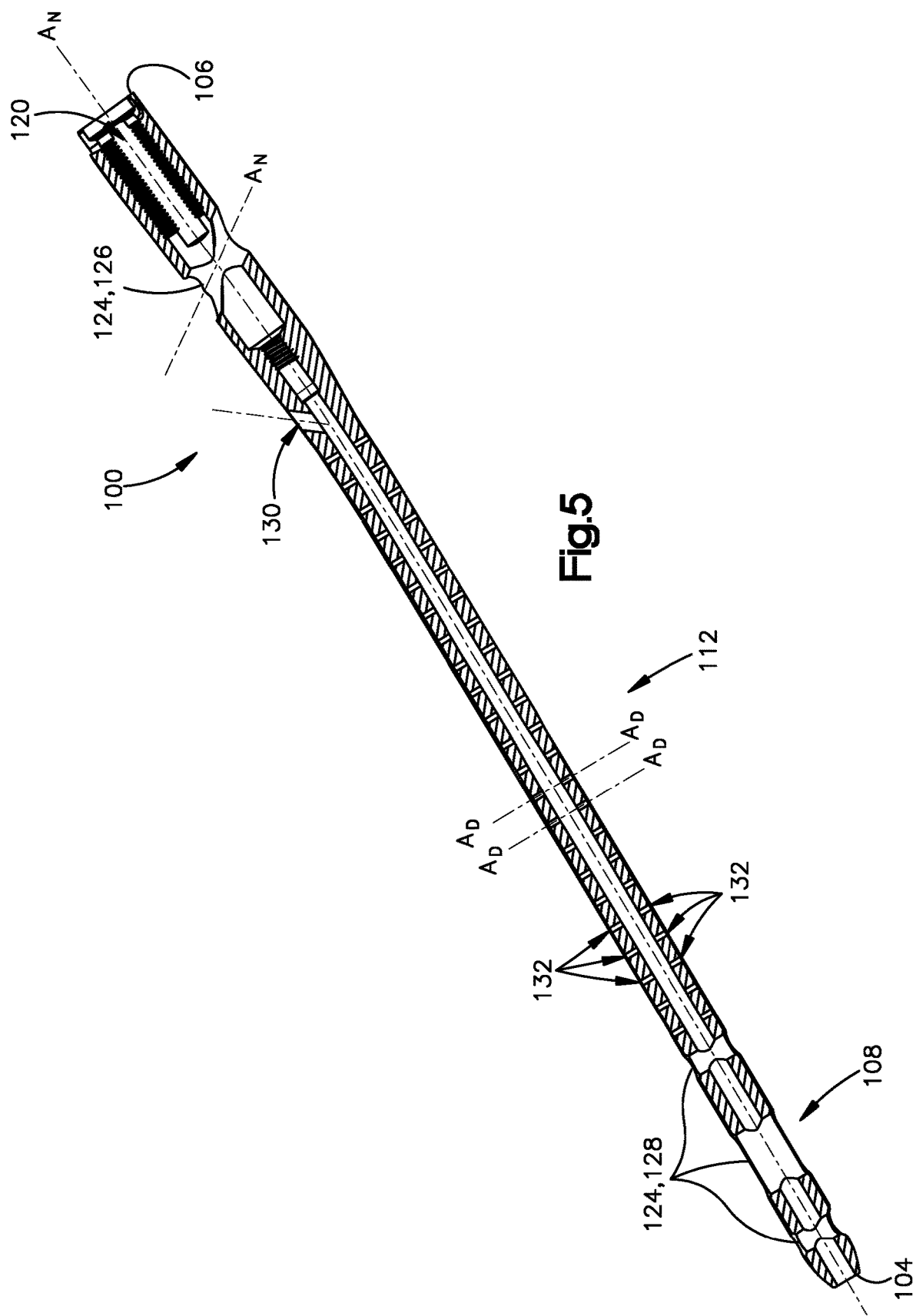
FIG. 5 shows a cross-sectional side view of an intramedullary nail according to another embodiment having an access hole that provides access to a cannulation in the intramedullary nail.

Commonly, an intramedullary nail is implanted by driving the nail into a medullary canal of a long bone such as a tibia, fibula, humerus, or femur. The nail is then secured to the bone by inserting bone anchors through the bone and into bone-anchor locking holes that are located at a proximal end and a distal end of the intramedullary nail. A bone anchor that extends through bone-anchor locking holes at the proximal end of the nail may pass through a cannulation that extends into the proximal end of the nail towards the distal end. In such case, the bone anchor intersects the cannulation, thereby restricting access to the cannulation from the proximal end of the nail. To provide access to the cannulation before or after insertion of the proximal bone anchor, an access hole can be provided in the intramedullary nail between the proximal end and the distal end of the nail. The access hole can provide access for a variety of procedures, including locating the bone-anchor locking hole or holes at the distal end that are hidden beneath the bone, or delivering cement or antibiotic to the nail.

Referring generally to the embodiments of FIGS. 1 to 4, an intramedullary nail 100 includes a nail body 102 having a distal end 104 and a proximal end 106 that are offset from one another. The distal end 104 can be considered to be an insertion end or leading end, and can define a first terminal or outermost end of the nail body 102. The proximal end 106 can be considered to be a trailing end and can define a second terminal or outermost end of the nail body 102.

The nail body 102 is elongate from the proximal end 106 to the distal end 104. For instance, the nail body 102 is substantially elongate along a central pathway that extends from the proximal end 106 to the distal end 104. In at least some embodiments, the central pathway can be defined by a central axis $A_N$ of the nail body 102 that extends from the proximal end 106 to the distal end 104. It will be appreciated that the central pathway or central axis $A_N$ of the nail body 102 can be straight or curved. Thus, the nail body 102 can be straight or curved as it extends along the central pathway or central axis $A_N$ from the proximal end 106 to the distal end 104. The intramedullary nail 100 can be inserted into a medullary canal of a long bone such that the central pathway or central axis $A_N$ extends along the length of the medullary canal.

The nail body 102 has a leading portion 108 and a trailing portion 110 that are offset from one another. The nail body 102 also has an intermediate portion 112 between the leading portion 108 and the trailing portion 110. The leading portion 108 can extend from the distal end 104 of the nail body 102 towards the proximal end 106 along a trailing direction T. Further, the trailing portion 110 can extend from the proximal end 106 towards the distal end 104 along an insertion direction I. For example, the leading portion 108 can extend from the distal end 104 to the intermediate portion 112, and the trailing portion 110 can extend from the proximal end 106 to the intermediate portion 112. It will be understood that the insertion direction I extends from the proximal end 106 towards the distal end 104, and the trailing direction T extends in a direction opposite the insertion direction I (i.e., from the distal end 104 towards the proximal end 106).

In at least some embodiments, the trailing portion 110 has a length $L_T$ that is less than or equal to one third of an overall length $L_O$ of the intramedullary nail 100. In at least some such embodiments, the trailing portion 110 has a length $L_T$ that is less than or equal to one quarter of the overall length $L_O$ of the intramedullary nail 100. Additionally or alternatively, in at least some embodiments, the leading portion 108 has a length $L_L$ that is less than or equal to one third of an overall length $L_O$ of the intramedullary nail 100. In at least some such embodiments, the leading portion 108 has a length $L_L$ that is less than or equal to one quarter of an overall length $L_O$ of the intramedullary nail 100.

The nail body 102 has an outer surface 114 that extends from the leading portion 108 to the trailing portion 110. For instance, the outer surface 114 can extend from the proximal end 106 to the distal end 104. The outer surface 114 can define an outer-most perimeter of the intramedullary nail 100. Further, the outer surface 114 can have any suitable cross-sectional shape as desired. For example, the outer surface 114 can be substantially circular in cross section along a plane that is substantially perpendicular to the central pathway or central axis $A_N$. Additionally or alternatively, the nail body 102 can define a plurality of recesses 116 that extend into the outer surface 114. The recesses 116 can be spaced circumferentially from one another around an outer perimeter of the nail body 102 and can be elongate as they extend between the leading portion 108 and the trailing portion 110 in accordance with the illustrated embodiments.

The nail body 102 has an inner surface 118 opposite the outer surface 114. Thus, the nail body 102 defines a tubular wall 122 between the inner surface 118 and the outer surface 114. The inner surface 118 defines a cannulation 120 that extends into the proximal end 106 in the insertion direction I. The cannulation 120 can extend to the leading portion 108. For example, the cannulation 120 can extend through the distal end 104. Alternatively, the cannulation 120 can terminate prior to the distal end 104 such as in the intermediate portion 112. The inner surface 118 can have a plurality of cross-sections along the central pathway or central axis $A_N$, each cross-section defined in a plane that is perpendicular to the central pathway or central axis $A_N$. The inner surface 118 in each cross-section can have any suitable cross-sectional shape as desired. For example, the inner surface 118 in each cross-section can define a cross-sectional shape that is closed such as a circle, oval, square, rectangle, or other shape.

The nail body 102 defines a plurality of bone-anchor through holes 124. Each bone-anchor through hole 124 is configured to receive a bone anchor that extends through the bone-anchor through hole 124 so as to attach the nail body 102 to a bone. In particular, each bone-anchor through hole 124 extends into the outer surface 114 and entirely through the nail body 102. For instance, each bone-anchor through hole 124 can extend into the outer surface 114 on a first side of the nail body 102 and out of the outer surface 114 on a second side of the nail body 102, opposite the first side. Thus, each bone-anchor through hole 124 can extend from an opening 124a on a first side of the nail body 102 to an opening 124b on the second side of the nail body 102. At least some of the bone-anchor through holes 124 can extend through the tubular wall 122 on a first side of the nail body 102 and through the tubular wall 122 on a second side of the nail body 102, opposite the first side.

Each bone-anchor through hole 124 extends through the nail body 102 along a central bone-anchor axis $A_B$ that is angled with respect to the central pathway or central axis $A_N$. For example, the central axis $A_N$ extends along a first direction adjacent each bone-anchor through hole 124, and each bone-anchor through hole 124 extends into the nail body along a central axis $A_B$ that extends along a second direction, the second direction forming a non-zero angle with the first direction. In some embodiments, each bone-anchor through hole 124 extends through the nail body 102 along a central axis $A_B$ that forms a non-zero angle, such as a right angle or an oblique angle, with the central pathway or central axis $A_N$. Each bone-anchor through hole 124 can be unthreaded or can include internal threading to receive external threading of a bone anchor.

The plurality of bone-anchor through holes 124 includes at least one proximal bone-anchor locking hole 126. Each of the at least one proximal bone-anchor locking hole 126 extends entirely through the trailing portion 110 of the nail body 102. In some embodiments, each of the at least one proximal bone-anchor locking hole 126 extends into the nail body 102 at a distance from the distal end 106 that is less than or equal to one third of the overall length $L_O$ of the intramedullary nail 100, while in other embodiments, each of the at least one proximal bone-anchor locking hole 126 extends into the nail body 102 at a distance from the distal end 106 that is less than or equal to one quarter of the overall length $L_O$ of the intramedullary nail 100. Although only one proximal bone-anchor locking hole 126 is shown, it will be understood that the nail body 102 can define a plurality of proximal bone-anchor locking holes 126. In such embodiments, the plurality of proximal bone-anchor locking holes 126 can be offset from one another along a longitudinal direction L that extends between the distal end 104 and the proximal end 106.

At least one proximal bone-anchor locking hole 126 can have an axis $A_B$ that is aligned along the longitudinal direction L with the axis $A_B$ of an adjacent proximal bone-anchor locking hole 126. Thus, the openings 124a and 124b of the proximal bone-anchor locking hole 126 can be aligned along the longitudinal direction L with the openings 124a or 124b of an adjacent proximal bone-anchor locking hole 126. Further, the central bone-anchor axis $A_B$ of each proximal bone-anchor locking hole 126 can be parallel to the central bone-anchor axis $A_B$ of an adjacent one of the proximal bone-anchor locking holes 126 or can be angularly offset from the central bone-anchor axis $A_B$ of an adjacent one of the proximal bone-anchor locking holes 126 such that the central bone-anchor axes $A_B$ converge on one side of the nail body 102 and diverge on the other side.

Alternatively, the axis $A_B$ of each proximal bone-anchor locking hole 126 can be angularly offset along the longitudinal direction L from the axis $A_B$ of an adjacent proximal bone-anchor locking hole 126. As such, the openings 124a and 124b of each proximal bone-anchor locking hole 126 can be out of alignment along the longitudinal direction L with the openings 124a and 124b of an adjacent proximal bone-anchor locking hole 126. In other words, the openings 124a and 124b of each proximal bone-anchor locking hole 126 at the outer surface 114 can be circumferentially offset from the openings 124a and 124b of an adjacent proximal bone-anchor locking hole 126 at the outer surface 114. Thus, the central bone-anchor axis $A_B$ of each proximal bone-anchor locking hole 126 can be at a non-zero angle relative to the central bone-anchor axis $A_B$ of an adjacent one of the proximal bone-anchor locking holes 126.

The plurality of bone-anchor through holes 124 also includes at least one distal bone-anchor locking hole 128. All of the at least one distal bone-anchor locking holes 128 are offset from all of the at least one proximal bone-anchor locking holes 126 along the longitudinal direction L. Each of the at least one distal bone-anchor locking hole 128 extends entirely through the leading portion 108 of the nail body 102. In some embodiments, each of the at least one distal bone-anchor locking hole 128 extends into the nail body 102 at a distance from the distal end 104 that is less than or equal to one third of the overall length $L_O$ of the intramedullary nail 100, while in other embodiments, each of the at least one distal bone-anchor locking hole 128 extends into the nail body 102 at a distance from the distal end 104 that is less than or equal to one quarter of the overall length $L_O$ of the intramedullary nail 100. Although a plurality of distal bone-anchor locking holes 128 is shown, it will be understood that the nail body 102 can define as few as one distal bone-anchor locking hole 128. In embodiments having a plurality of distal bone-anchor locking holes 128, the plurality of distal bone-anchor locking holes 128 can be offset from one another along the longitudinal direction L.

Each distal bone-anchor locking hole 128 can have an axis $A_B$ that is aligned along the longitudinal direction L with the axis $A_B$ of an adjacent distal bone-anchor locking hole 128. Thus, the openings 124a and 124b of the distal bone-anchor locking hole 128 can be aligned along the longitudinal direction L with the openings 124a and 124b of the adjacent distal bone-anchor locking hole 128. Further, the central bone-anchor axis $A_B$ of each distal bone-anchor locking hole 128 can be parallel to the central bone-anchor axis $A_B$ of an adjacent one of the distal bone-anchor locking holes 128 or can be angularly offset from the central bone-anchor axis $A_B$ of an adjacent one of the distal bone-anchor locking holes 128 such that the central bone-anchor axes $A_B$ converge on one side of the nail body 102 and diverge on the other side.

Alternatively, the axis $A_B$ of each distal bone-anchor locking hole 128 can be angularly offset from the axis $A_B$ of an adjacent distal bone-anchor locking hole 128 along the longitudinal direction L. As such, the openings 124a and 124b of each distal bone-anchor locking hole 128 can be out of alignment along the longitudinal direction L with the openings 124a and 124b of an adjacent distal bone-anchor locking hole 128. In other words, the openings 124a and 124b of each distal bone-anchor locking hole 128 can be circumferentially offset from the openings 124a and 124b of an adjacent distal bone-anchor locking hole 128. Thus, the central bone-anchor axis $A_B$ of each distal bone-anchor locking hole 128 can be at a non-zero angle relative to the central bone-anchor axis $A_B$ of an adjacent one of the distal bone-anchor locking holes 128.

Moreover, the axis $A_B$ of at least one distal bone-anchor locking hole 128 can be aligned with the axis $A_B$ of a proximal bone-anchor locking hole 126 along the longitudinal direction L such that the openings 124a and 124b of the distal bone-anchor locking hole 128 are aligned with the openings 124a and 124b of the proximal bone-anchor locking hole 126 along the longitudinal direction L. The central bone-anchor axis $A_B$ of a distal bone-anchor locking hole 128 can be parallel to the central bone-anchor axis $A_B$ of a proximal bone-anchor locking hole 126 or can be angularly offset from the central bone-anchor axis $A_B$ of an adjacent one of the proximal bone-anchor locking holes 126 such that the central bone-anchor axes $A_B$ converge on one side of the nail body 102 and diverge on the other side.

Alternatively, the axis $A_B$ of at least one distal bone-anchor locking hole 128 can be angularly offset from the axis $A_B$ of an adjacent proximal bone-anchor locking hole 126. As such, the openings 124a and 124b of the distal bone-anchor locking hole 128 can be out of alignment with the openings 124a and 124b of the proximal bone-anchor locking hole 126 along the longitudinal direction L. In other words, the openings 124a and 124b of the distal bone-anchor locking hole 128 can be circumferentially offset from the openings 124a and 124b of an adjacent proximal bone-anchor locking hole 126. Thus, the central bone-anchor axis $A_B$ of the distal bone-anchor locking hole 128 can be at a non-zero angle relative to the central bone-anchor axis $A_B$ of the proximal bone-anchor locking hole 126.

The nail body 102 defines an access hole 130 between the leading portion 108 and the trailing portion 110. For example, the nail body 102 can define the access hole 130 at the intermediate portion 112. Thus, the access hole 130 can be between all of the at least one distal bone-anchor locking holes 128 on the leading portion 108 and all of the at least one proximal bone-anchor locking holes 126 on the trailing portion 110. In some embodiments, the nail body 102 can be devoid of any distal bone-anchor locking holes 128 between the access hole 130 and the trailing portion 110. Additionally or alternatively, the nail body 102 can be devoid of any proximal bone-anchor locking holes 126 between the access hole 130 and the leading portion 108. Thus, in some embodiments, the intermediate portion 112 can be devoid of any bone-anchor through holes. The access hole 130 can extend into the nail body 102 at a location that is closer to the proximal end 106 than the distal end 104. For example, the access hole 130 can extend into the nail body 102 between the trailing portion 110 and a midpoint of the intramedullary nail 100. As another example, the access hole 130 can extend into the nail body 102 at a distance D from the proximal end 106 that is less than one third of the overall length $L_O$ of the intramedullary nail 100. As yet another example, the access hole 130 can extend into the nail body 102 at a distance D from the proximal end 106 that is less than one fourth of the overall length $L_O$ of the intramedullary nail 100. The nail body 102 can be devoid of bone-anchor locking holes between the access hole 130 and a midpoint of the central axis $A_N$.

The access hole 130 extends only partially through the nail body 102. For instance, the access hole 130 extends along an access hole central axis $A_H$ and into the outer surface 114 between the leading portion 108 and the trailing portion 110. Further, the access hole 130 extends through the inner surface 118 such that the access hole 130 terminates at the cannulation 120 and is in communication with the cannulation 120. In other words, the access hole 130 can extend through the tubular wall 122 on a first side of the nail body 102 and terminate at the tubular wall 122 on a second of the nail body 102, opposite the first side, without extending through the tubular wall 122 on the second side. Thus, the central axis $A_H$ intersects the tubular wall 122 on the second side of the nail body 102. Further, the nail body 102 can define an outer opening 130a at the outer surface 114 and an inner opening 130b at the inner surface 118, and the access hole 130 can extend from the outer opening 130a to the inner opening 130b.

The central axis $A_H$ of the access hole 130 can be aligned with the at least one of a proximal bone-anchor locking hole 126 and a distal bone-anchor locking hole 128 along the longitudinal direction L. Thus, the outer opening 130a of the access hole 130 can be aligned with an opening 124a or 124b of at least one of a proximal bone-anchor locking hole 126 and a distal bone-anchor locking hole 128 along the longitudinal direction L. Alternatively, the central axis $A_H$ of the access hole 130 can be angularly offset from the central axis $A_B$ of at least one of a proximal bone-anchor locking hole 126 and a distal bone-anchor locking hole 128 along the longitudinal direction L. Thus, the outer opening 130a of the access hole 130 can be out of alignment with the openings 124a and 124b of the proximal bone-anchor locking hole 126 and/or distal bone-anchor locking hole 128 along the longitudinal direction L.

The access hole 130 extends into the nail body 102 along an access-hole central axis $A_H$. The nail-body central axis $A_N$ can extend along a first direction at a location adjacent the access hole 130, and the access hole central axis $A_H$ can extend along a second direction that forms a non-zero angle with the first direction. In some embodiments, and with specific reference to FIGS. 1 and 2, the second direction can form an oblique angle with the first direction. Further, in some such embodiments, the access-hole central axis $A_H$ can be angled with respect to the central pathway or central axis $A_N$. In particular, the access hole 130 can extend into the nail body 102 along an access-hole central axis $A_H$ that forms an oblique angle with the central pathway or central axis $A_N$. It will be understood, however, that in some embodiments the access-hole central axis $A_H$ need not intersect the central axis $A_N$. The access hole 130 can be angled towards the distal end 104 as the access hole 130 extends from the outer surface 114 to the inner surface 118. As such, the inner surface 131 that defines the access hole 130 is configured to guide an instrument (discussed below) towards the leading portion 108 as the instrument is inserted into the access hole 130.

In other embodiments, and with specific reference to FIGS. 3 and 4, the nail-body central axis $A_N$ can extend along a first direction at a location adjacent the access hole 130, and the access hole central axis $A_H$ can extend along a second direction that forms a right angle with the first direction. In some such embodiments, the access hole 130 can form a right angle with the central pathway or central axis $A_N$. An instrument (see e.g., 602 of FIG. 6 below) can be inserted into the access hole 130 along a path that is angled towards the leading portion 108 as the path extends from the outer surface 114 to the inner surface 118 so as to direct the instrument towards the leading portion 108 as the instrument is inserted into the access hole 130. In other words, rather than the access hole 130 directing the instrument towards the leading portion 108, another device such as an aiming sleeve (see e.g., 400 of FIG. 6) or the user can angle the instrument as the instrument is inserted into the access hole 130 so as to guide the instrument towards the leading portion 108. In some embodiments, the access hole 130 can be angled towards the leading portion 108 and an aiming sleeve 400 and the access hole 130 together can guide the instrument towards the leading portion 108.

The access hole 130 can have any suitable cross-sectional shape in a plane that is perpendicular to the access-hole central axis $A_H$. For example, and with specific reference to FIGS. 1 and 2, the access hole 130 can have a cross-sectional shape that is substantially circular in a plane that is perpendicular to the access-hole central axis $A_H$. As another example, and with specific reference to FIGS. 3 and 4, the access hole 130 can have a cross-sectional shape that is substantially oblong in a plane that is perpendicular to the access-hole central axis $A_H$.

Turning now to FIG. 5, in some embodiments, the nail body 102 can define a plurality of discharge holes 132, each extending into the nail body 102 along a discharge-hole central axis $A_D$. In some embodiments, each discharge hole 132 can have a cross-sectional dimension (such as a diameter) in a plane that is perpendicular to its discharge-hole central axis $A_D$ that is less than a cross-sectional dimension of each bone-anchor through hole 124. Each discharge hole 132 can be considered a weep hole or pin hole.

Each discharge hole 132 is configured to permit a flowable, biocompatible substance such as a gas, liquid, or gel to discharge out of the cannulation 120 to the surrounding tissue. The flowable substance can be a viscous substance. For example, in some embodiments, a medicine such as an antibiotic can be dispensed through the access hole 130 and into the cannulation 120. The medicine can then be permitted to dispense through the discharge holes 132 to the fracture site in the bone so as to promote healing of the fracture. In such embodiments, at least some of the discharge holes 132 preferably extend into the outer surface 114 of the nail body 102 at a location that aligns with a fracture site.

As another example, in some embodiments, a bonding adhesive or cement can be dispensed through the access hole 130 and into the cannulation 120. The adhesive or cement can then be permitted to dispense through the discharge holes 132 and into the bone so as to bond the nail body 102 to the bone. In such embodiments, at least some of the discharge holes 132 preferably extend into the outer surface 114 at a location that is spaced from the fracture site.

Each discharge hole 132 can extend into the outer surface 114 between the leading portion 108 and the trailing portion 110. For example, each discharge hole 132 can extend into the intermediate portion 112. Thus, each discharge hole 132 can be between all of the at least one distal bone-anchor locking holes 128 on the one end and all of the at least one proximal bone-anchor locking holes 126 on the other end. Thus, in some embodiments, the nail body 102 can be devoid of any distal bone-anchor locking holes 128 between the discharge holes 132 and the trailing portion 110. Additionally or alternatively, the nail body 102 can be devoid of any proximal bone-anchor locking holes 126 between the discharge holes 132 and the leading portion 108.

Each discharge hole 132 can extend only partially through the nail body 102. For instance, each discharge hole 132 can extend along a discharge-hole central axis $A_D$ and into the outer surface 114 between the leading portion 108 and the trailing portion 110 and terminate at the cannulation 120, without extending entirely through the intramedullary nail 100. Further, each discharge hole 132 can extend through the inner surface 118 such that the discharge hole 132 is in communication with the cannulation 120. In other words, each discharge hole 132 can extend through the tubular wall 122 on a first side of the nail body 102 and terminate at the tubular wall 122 on a second side of the body 102, opposite the first side, without extending through the tubular wall 122 on the second side. Alternatively, each discharge hole 132 can extend entirely through the nail body 102, such that the discharge hole 132 extends through the tubular wall 122 on a first and second sides of the nail body 102.

Each discharge hole 132 can extend into the nail body 102 along a discharge-hole central axis $A_D$ that is angled with respect to the central pathway or central axis $A_N$. For example, each discharge hole 132 can extend through the nail body 102 along a discharge-hole central axis $A_D$ that forms a non-zero angle, such as a right angle or an oblique angle, with the central pathway or central axis $A_N$.

Figure 6:
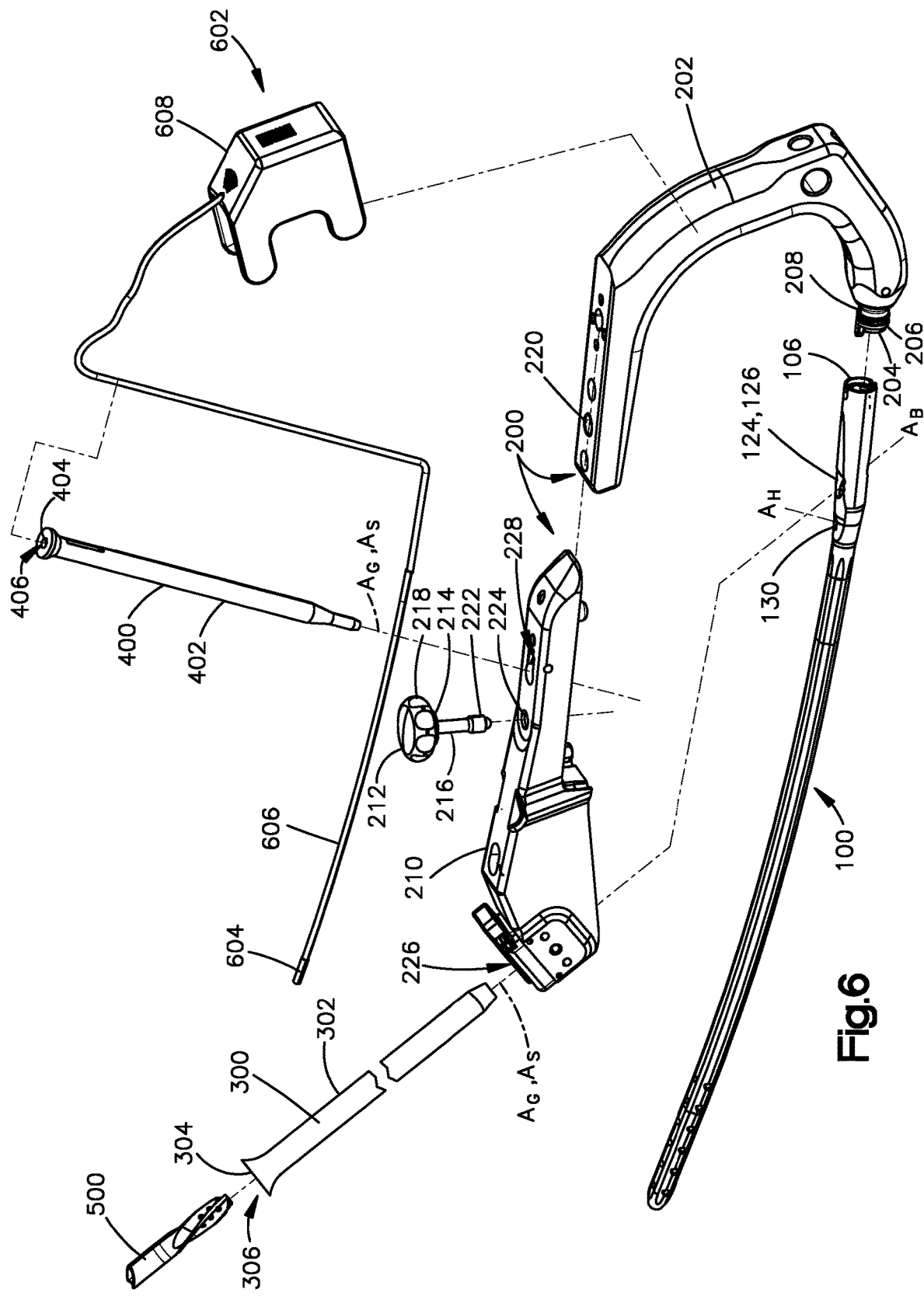
FIG. 6 shows an exploded perspective view of an intramedullary nail with an aiming system and a targeting instrument according to one embodiment.

Turning now to FIG. 6, an intramedullary nail insertion system is shown with an intramedullary nail 100, an aiming system 200, and a targeting instrument 602. The aiming system 200 can include any combination of one or more, up to all, of (i) a handle 202, (ii) an aiming arm 210, (iii) a bone-anchor aiming sleeve 300, and (iv) an access-hole aiming sleeve 400. The aiming system 200 is configured to align tools or instruments with at least one of a proximal bone-anchor locking hole 126 and the access hole 130. For example, when the aiming system 200 is attached to the intramedullary nail 100, the aiming system 200 can align at least one of a drill bit (not shown) and a bone anchor 500 with the at least one proximal bone-anchor locking hole 126 so as to guide the at least one of a drill bit (not shown) and the bone anchor 500 towards the at least one proximal bone-anchor locking hole 126. The bone anchor 500 can be a locking screw or any other suitable bone anchor. In addition or alternatively, when the aiming system 200 is attached to the intramedullary nail 100, the aiming system 200 can align at least one of a drill bit (not shown) and an instrument (e.g., 602 of FIG. 6) with the access hole 130 so as to guide the at least one of a drill bit (not shown) and instrument towards the access hole 130. Although one embodiment of an aiming system 200 is shown, it will be understood that other configurations of aiming systems can be employed. For instance, at least one of the handle 202 and aiming arm 210 can be configured in a manner other than that shown.

The handle 202 is configured to be held by an operator (human or machine) as the operator guides and forces the intramedullary nail 100 into the medullary canal of the bone. The handle 202 can include a connection end 204 configured to connect to the proximal end 106 of the intramedullary nail 100. The connection end 204 can include an engagement feature configured to couple to an engagement feature at the proximal end 106 of the intramedullary nail 100. For example, in one embodiment, the engagement feature of the handle 202 can include a shaft 206 having external threading 208 thereon, and the engagement feature of the intramedullary nail 100 can include internal threading 134 (see FIG. 2) on the inner surface 118 of the cannulation 120 of the intramedullary nail 100 at the proximal end 106. The shaft 206 can be sized and configured to be received in the cannulation 120 at the proximal end 106 of the intramedullary nail 100 such that the external threading 208 engages the internal threading 134 of the intramedullary nail 100. In alternative embodiments, the engagement features of the handle 202 and the intramedullary nail 100 can be engagement features other than the internal and external threading shown, the other engagement features being suitable for coupling the handle 202 to the intramedullary nail 100.

The at least one aiming arm 210 can be fixedly or removably attached to the handle 202 via any suitable fastener. Alternatively, the handle 202 can be monolithic with the aiming arm 210 such that the handle 202 and aiming arm 210 form a one-piece structure. The aiming system 200 can include a coupler 212 that removably attaches the aiming arm 210 to the handle 202. In one embodiment, the coupler 212 can have an abutment surface 214 and a shaft 216 that extends from the abutment surface 214 to a distal end of the shaft 216. The abutment surface 214 can be defined by a handgrip 218. The shaft 216 can have an engagement feature configured to engage an engagement feature of a bore 220 of the handle 202. Further, the shaft 216 is sized and configured to extend through a bore 224 of the aiming arm 210 into the bore 222 of the handle 202 such that the aiming arm 210 is trapped between the abutment surface 214 and the handle 202. In one example, the engagement feature of the shaft 216 can be external threading and the engagement feature of the bore 220 can be internal threading that is configured to engage the external threading of the shaft 216.

The aiming system 200 can define a guide hole 226 that is configured to guide at least one a drill bit (not shown) and the bone anchor 500 towards the at least one proximal bone-anchor locking hole 126. The guide hole 226 can have a central axis $A_G$ that is substantially aligned with the central axis $A_B$ of the at least one proximal bone-anchor locking hole 126 when the aiming system 200 is attached to the intramedullary nail 100. In addition or alternatively, the aiming system 200 can define a guide hole 228 that is configured to guide at least one of a drill bit (not shown) and an instrument (e.g., 602 of FIG. 6) towards the access hole 130. The guide hole 228 has a central axis $A_G$ that is substantially aligned with the central axis $A_H$ of the access hole 130 when the aiming system 200 is attached to the intramedullary nail 100.

The bone-anchor aiming sleeve 300 has a tubular body that includes an outer surface 302 and an inner surface 304. The outer surface 302 defines an outer perimeter of the sleeve 300 and is sized and configured to conform to the guide hole 226. The inner surface 304 is opposite the outer surface 302 and defines a cannulation 306 that extends entirely through the sleeve 300. The cannulation 306 is sized to receive at least one of a drill bit (not shown) and the bone anchor 500. When the sleeve 300 is received in the guide hole 226 and the aiming system 200 is attached to the intramedullary nail 100, a central axis $A_S$ of the sleeve 300 can be substantially aligned with the central axis $A_G$ of the guide hole 226 and the central axis $A_B$ of the at least one proximal bone-anchor locking hole 126. As such, the sleeve 300 is positioned and configured to guide at least one of a drill bit (not shown) and the bone anchor 500 towards the at least one proximal bone-anchor locking hole 126. It will be understood that, in alternative embodiments, the sleeve 300 can be integral with the aiming arm 210 or can be omitted.

Similarly, the access-hole aiming sleeve 400 has a tubular body that includes an outer surface 402 and an inner surface 404. The outer surface 402 defines an outer perimeter of the sleeve 400 and is sized and configured to conform to the guide hole 228. The inner surface 404 is opposite the outer surface 402 and defines a cannulation 406 that extends entirely through the sleeve 400. The cannulation 406 is sized to receive at least one of a drill bit (not shown) and an instrument (e.g., 602 of FIG. 6). When the sleeve 400 is received in the guide hole 228 and the aiming system 200 is attached to the intramedullary nail 100, a central axis $A_S$ of the sleeve 400 can be substantially aligned with the central axis $A_G$ of the guide hole 228 and the central axis $A_H$ of the access hole 130. As such, the sleeve 400 is positioned and configured to guide at least one of a drill bit (not shown) and the instrument towards the access hole 130. It will be understood that, in alternative embodiments, the sleeve 400 can be integral with the aiming arm 210 or can be omitted.

Figure 9:
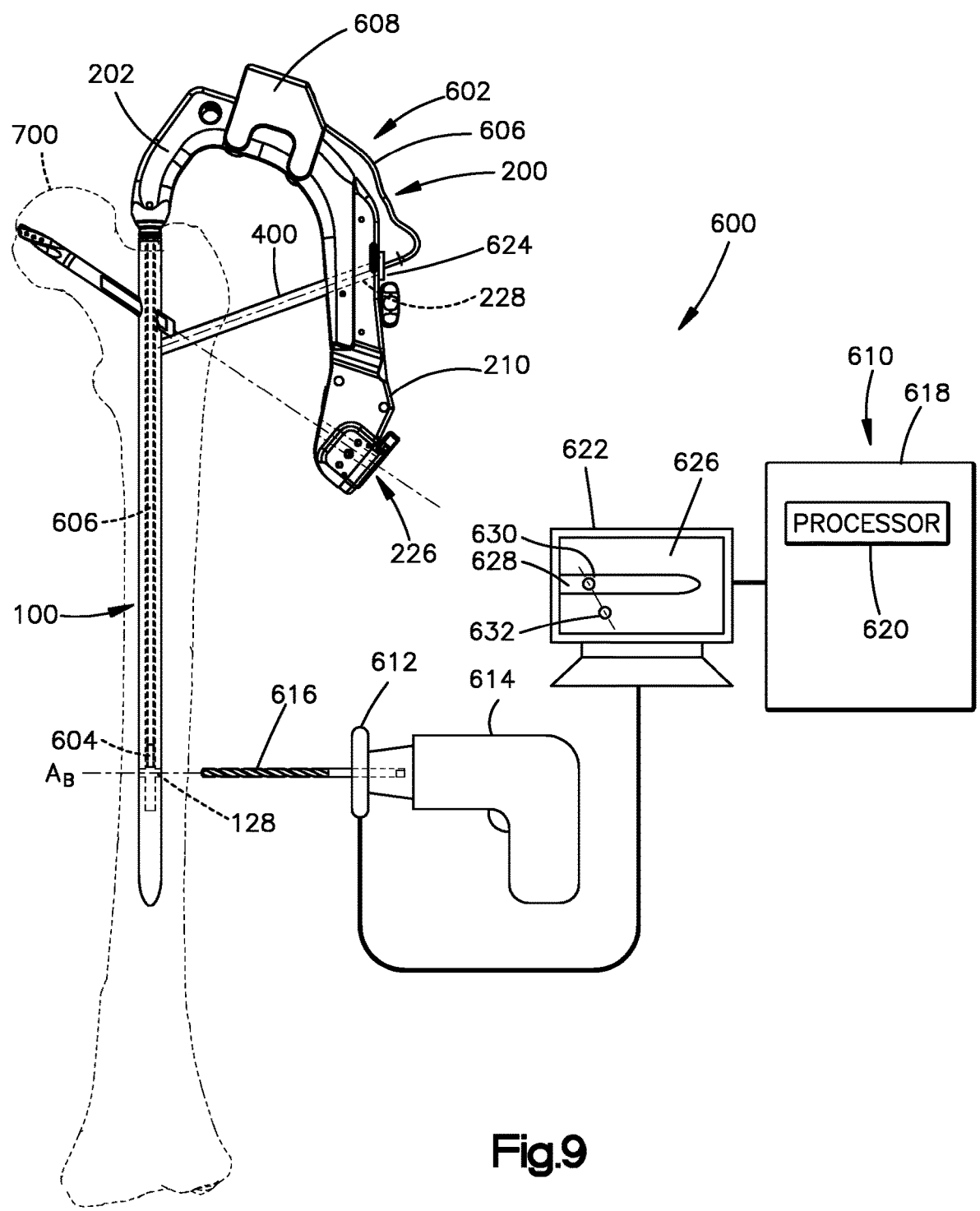
FIG. 9 shows a schematic diagram of an aiming system attached to an intramedullary nail that is received in a medullary canal of a bone and a targeting system used to locate a distal bone-anchor locking hole of an intramedullary nail.

Referring now to FIGS. 6 and 9, embodiments of the disclosure can include a targeting system 600 that can be used to detect a location of at least one of a proximal bone-anchor locking hole 126 and a distal bone-anchor locking hole 128 hidden beneath the surface of the bone 700. The targeting system 600 can be implemented as described in U.S. Pat. No. 8,623,023, the teachings of which are hereby incorporated by reference as if set forth in their entirety herein. The targeting system 600 can include a probe 602 having a locator 604 such as a magnet or sensor and a cable 606 that supports the locator 604. In embodiments that employ a sensor, the sensor can be a six degree of freedom sensor, although it will be understood that other sensors can be used. At least a portion of the probe 602, including the locator 604 and the cable 606, is sized to be received through the access hole 130 and into the cannulation 120 to a location that is adjacent a select bone-anchor locking hole.

The probe 602 can optionally include a wireless communicator 608 that communicates with a computing device 610 positioned outside of the body. Alternatively, the probe 602 can be connected to the computing device 610 via a cable such that communications between the probe 602 and the computing device 610 occur over the cable. The wireless communicator 608 can include an antenna (not shown), a communications circuit (not shown) coupled to the antenna, and a power source such as a battery that can power at least one of the wireless communicator 608 and the locator 604. In one example, the wireless communicator 608 can be attached to a proximal end of the cable 602 and the locator 604 can be attached to a distal end of the cable 602.

The targeting system 600 can further include at least one of a computing system 610, a landmark identifier 612, and a cutting instrument 614 such as a drill having a drill bit 616. The landmark identifier 612 is used to detect a location of at least one of a proximal bone-anchor locking hole 126 and a distal bone-anchor locking hole 128. The landmark identifier 612 can include one or more small mobile inductive sensors or can include a field generator that includes one or more induction coils that generate an electromagnetic field. The computing system 610 can include a processor 620 and a feedback device 622 that provides to the user at least one of (i) a visual feedback (e.g., via a monitor or lights), (ii) an audio feedback (e.g., via a speaker), and (iii) a tactile feedback. The processor 620 and the feedback device 622 can be implemented in separately or the feedback device 622 can be implemented in a shared housing 618 with the processor 620.

Figure 7:
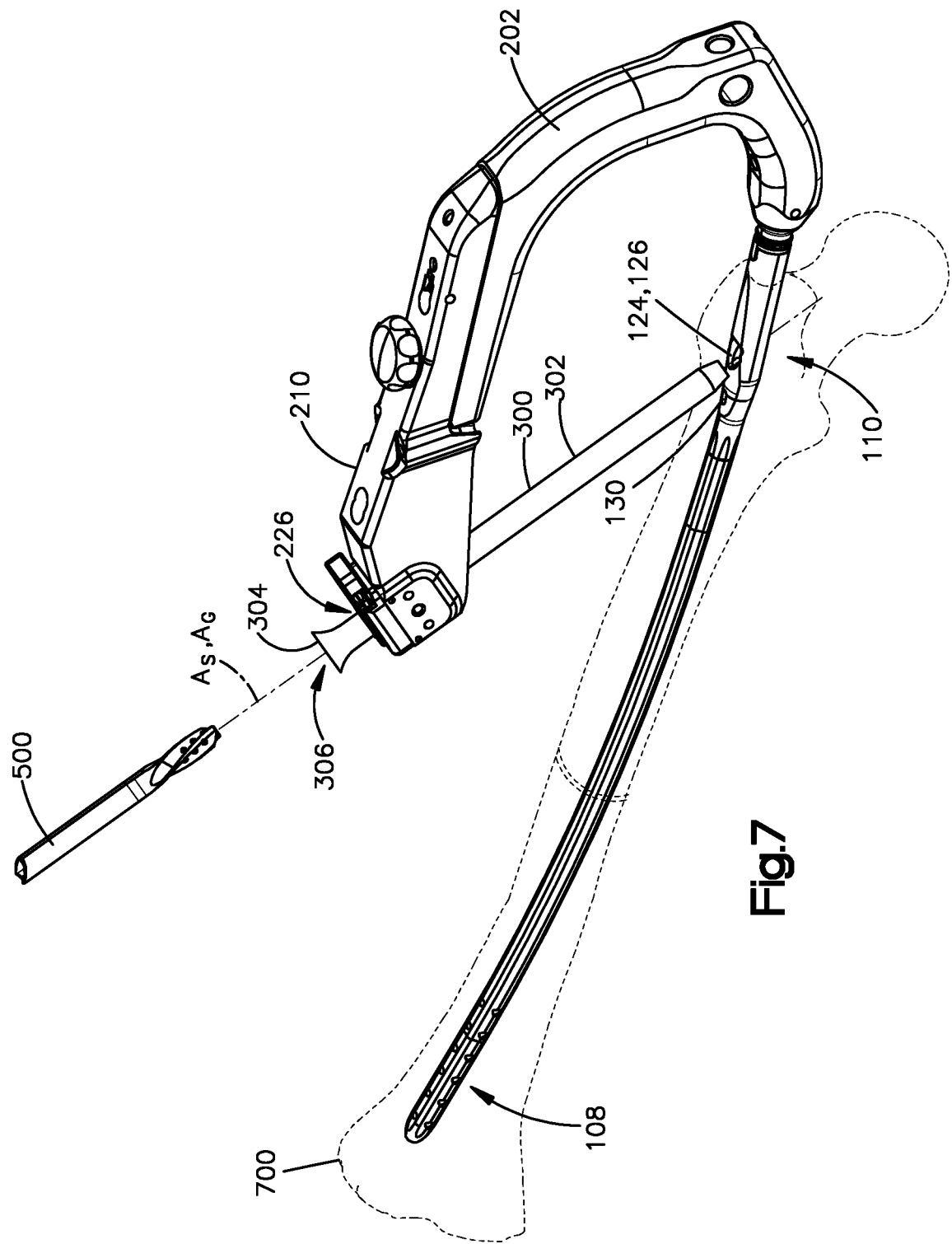
FIG. 7 shows a perspective view of an aiming guide attached to an intramedullary nail that is received in a medullary canal of a bone, the aiming guide supporting a bone-anchor aiming sleeve receiving a drill bit.

Turning now to FIGS. 7 to 10, a method 800 of implanting the intramedullary nail 100 will now be described. In step 802 of FIG. 10, the intramedullary nail 100 is inserted into the medullary canal of a bone 700 such that the intramedullary nail 100 is elongate along the medullary canal from the leading portion 108 of the intramedullary nail 100 to the trailing portion 110 of the intramedullary nail 100 as shown in FIG. 7. In one embodiment, the handle 202 of the aiming system 200 is coupled to the proximal end 106 of the intramedullary nail 100, and the operator holds onto the handle 202 to drive the intramedullary nail 100 into the medullary canal of the bone 700. The aiming arm 210 can be attached to the handle 202 before or after the nail 100 is driven into the bone.

Optionally, in step 804, a proximal bone anchor 500 can be inserted into at least one proximal bone-anchor locking hole 126 such that the proximal bone anchor 500 extends through the cannulation 120 of the intramedullary nail 100. As a result, the bone anchor 500 intersects the cannulation 120 so as to at least partially obstruct the proximal end of the cannulation 120. According to one embodiment, step 804 can be performed as follows and with reference to FIG. 7. The aiming arm 210 is attached to the handle 202 (if not already attached). The bone-anchor aiming sleeve 300 is received in the guide hole 226 of the aiming system 200 such that the central axis $A_S$ of the sleeve 300 is substantially aligned with both the central axis $A_G$ of the guide hole 226 and the central axis $A_B$ of the at least one proximal bone-anchor locking hole 126. A cut is made in the skin of the patient (before or after receiving the sleeve 300) at a point where the central axis $A_G$ of the guide hole 226 intersects the skin, and the sleeve 300 can be advanced into the skin towards the bone 700. A cutting instrument, such as a drill bit 616 of a drill 616 (shown in FIG. 9), can then be inserted into the bone-anchor aiming sleeve 300 and guided towards the proximal bone-anchor locking hole 126 so as to cut a bore that extends into the bone to the proximal bone-anchor locking hole 126. A bone anchor 500 such as a locking screw or other suitable bone anchor is driven through the bore in the bone and into the proximal bone-anchor locking hole 126 so as to secure the proximal end 106 of the intramedullary nail 100 to the bone 700.

Figure 8:
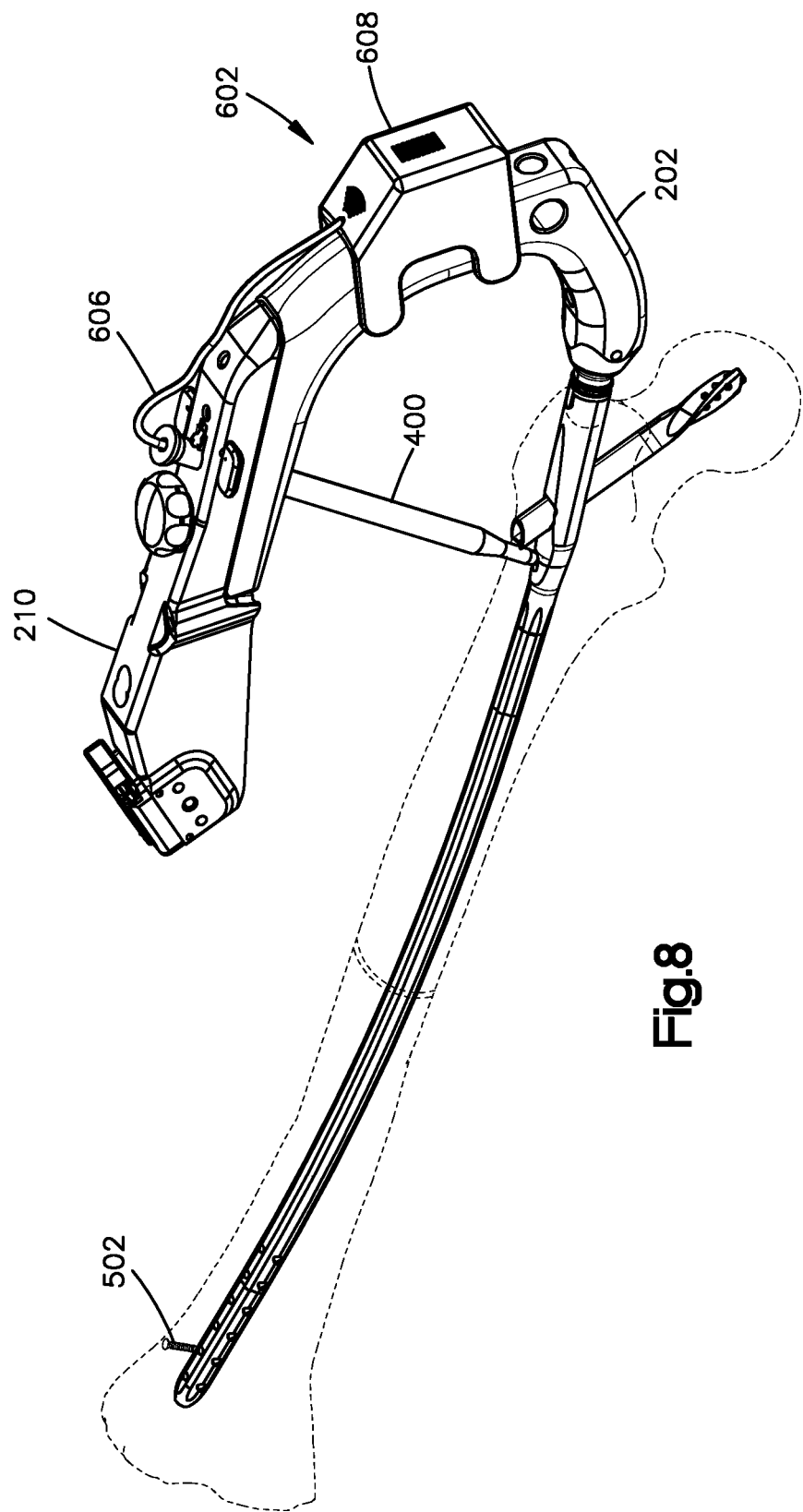
FIG. 8 shows a perspective view of an aiming guide attached to an intramedullary nail that is received in a medullary canal of a bone, the aiming guide supporting an access-hole aiming sleeve and a probe.
Figure 10:
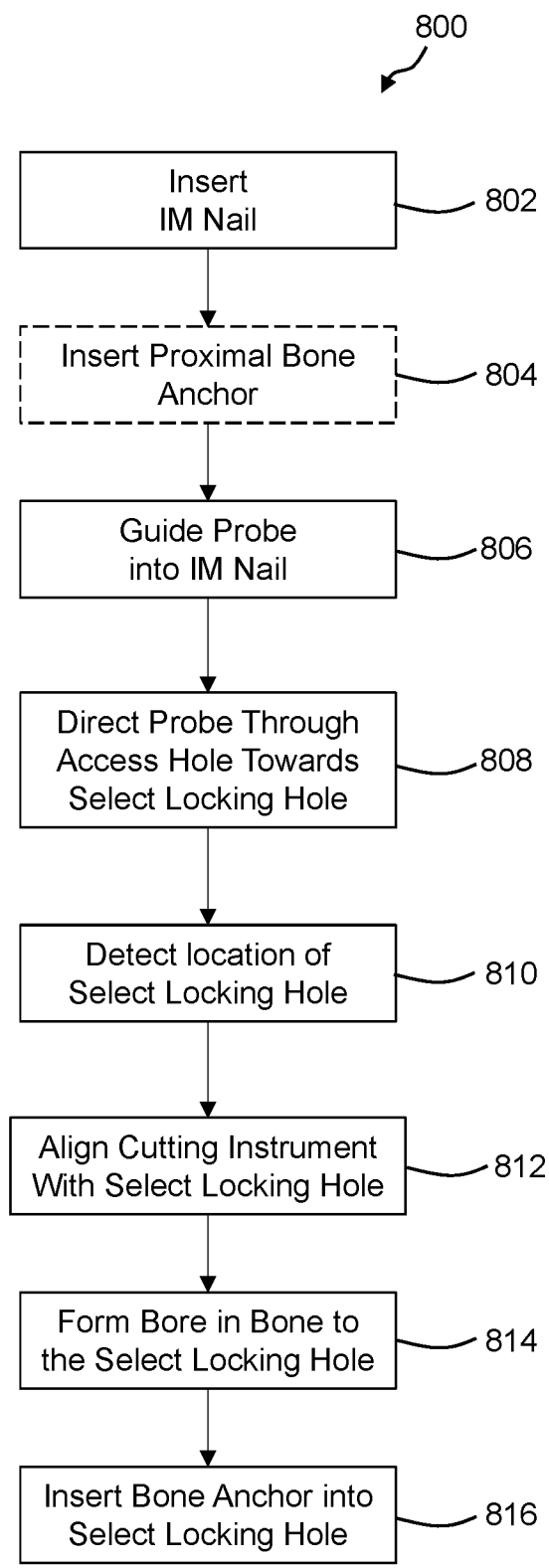
FIG. 10 shows a simplified flow diagram of a method of implanting an intramedullary nail according to one embodiment.

Referring more specifically to FIGS. 8-10, in step 806, the probe 602 is guided into the cannulation 120 of the intramedullary nail 100 through the access hole 130 that extends into the outer surface 114 of the intramedullary nail 100 between the at least one proximal bone-anchor locking hole 126 and the at least one distal bone-anchor locking hole 128. According to one embodiment, step 806 can be performed as follows and with reference to FIGS. 8 and 9. The aiming sleeve 400 is received in the guide hole 228 of the aiming system 200 (assuming it is not already received or is not integral with the aiming arm 210) such that the central axis $A_S$ of the sleeve 400 is substantially aligned with both the central axis $A_G$ of the guide hole 228 and the central axis $A_B$ of the access hole 130. A cut is made in the skin of the patient (before or after receiving the sleeve 400) at a point where the central axis $A_G$ of the guide hole 228 intersects the skin, and the sleeve 400 can be advanced into the skin towards the bone 700. A cutting instrument is then advanced through the sleeve 400 and towards the bone 700 so as to cut a bore in the bone 700 that extends to the access hole 130. Preferably, the bore in the bone has a central axis that is substantially aligned with the central axis $A_H$ of the access hole 130. The locator 604 of the probe 602 is then guided through the aiming sleeve 400 and into the access hole 130 of the intramedullary nail 100 by pushing the cable 606 into the aiming sleeve 400.

In step 808, the probe 602 is directed along the cannulation 120 of the intramedullary nail 100 towards a select locking hole of the proximal and distal bone-anchor locking holes 126 and 128 until the locator 604 of the probe 602 is proximate to the select locking hole. In embodiments in which the proximal bone anchor 500 is inserted prior to step 806, the select locking hole can be at least one distal bone-anchor locking hole 126. In other embodiments, where the proximal bone anchor 500 is not inserted prior to step 806, the select locking hole can be either a proximal bone-anchor locking hole 126 or a distal bone-anchor locking hole 128. The probe 602 can be directed a predetermined distance into the cannulation 120 so as to place the locator 604 adjacent the select locking hole. For example, a stop 624 (FIG. 9) can abut the aiming system 200 (e.g., a proximal end of the sleeve 400 or the aiming arm 210) when the locator 604 has traveled the predetermined distance into the intramedullary nail 100. Alternatively, markings on the cable 606 can be used to determine when the locator 604 has traveled the predetermined distance into the intramedullary nail 100.

In step 810, and with reference to FIGS. 9 and 10, a location of the select locking hole is detected based on a position of the locator 604. In some embodiments, the processor 620 can receive signals from at least one of (i) the locator 604 and (ii) the landmark identifier 612, and determine, based on the received signals, a current position and orientation of the landmark identifier 612 relative to the locator 604.

In the following description, one example method for detecting the location of the select locking hole is described; however, it will be understood that other methods are possible. The processor 620 can use a feature of a signal received from the locator 604 to determine a distance of the landmark identifier 612 from the locator 604. The feature can be, in one example, example, one or more electrical currents induced in the locator 604. Additionally or alternatively, the processor 620 can determine, based on the received signals, an orientation of a magnetic moment of a field generated by the landmark identifier 612. For example, the locator 604 can transmit a signal indicative of a current value and an identifier that indicates which of a plurality of induction coils of the locator 604 produced the associated current value.

The processor 620 can compare the current values received from the locator 604 (wirelessly or via a wire) with reference values associated with each of the induction coils of the landmark identifier 612 to determine differences between the received values and the reference values. The reference values can be values of induced current associated with a reference field generation signal, a reference position, and a reference orientation of the landmark identifier 612. The processor 620 can use these determined differences between the received and reference values to determine a difference in position and orientation of the landmark identifier 612 from the reference position and orientation based on any determined difference in the magnetic field generated by the landmark identifier 612 from the reference field. The processor 620 can determine a current position and orientation of the landmark identifier 612 relative to the locator 604 based on the difference in position and orientation of the landmark identifier 612 and the reference position and orientation.

The processor 620 can use the current distance and orientation of the landmark identifier 612 relative to the locator 604 to determine the current distance of the landmark identifier 612 from the distal bone-anchor locking hole 128 and the current relative orientation of the magnetic moment of the generated magnetic field relative to the central axis $A_B$ of the distal bone-anchor locking hole 128. For example, the processor 620 can determine the current distance and relative orientation of the landmark identifier 612 relative to the distal bone-anchor locking hole 128 based on a known position and orientation of the distal bone-anchor locking hole 128 relative to the locator 604. The processor 620 also determines a current position of the drill 614, including the drill bit 616, from the distal bone-anchor locking hole 128 as well as a current orientation of the drill 614 and the drill bit 616 relative to the central axis $A_H$ of the distal bone-anchor locking hole 128 based on a known position and orientation of the drill 614 and the drill bit 616 relative to the location of the landmark identifier 612 and the magnetic moment of the field generated by the landmark identifier 612. A longitudinal axis of the drill bit 616 is coaxial with the magnetic moment of the magnetic field generated by the landmark identifier 612.

With continued reference to FIGS. 9 and 10, in step 812, the cutting instrument is aligned with the select locking hole based on the detected location of the select locking hole. The cutting instrument and select locking hole can be aligned using feedback generated by the processor 620 and provided to the operator by the feedback device 622. For example, the processor 620 of the computing device 610 can generate a graphical user interface based on the determined current position and orientation of the drill 614 and the drill bit 616 relative to the distal bone-anchor locking hole 128, or based on a current position and orientation of another tool relative to another landmark. The graphical user interface can include a representative image 628 of the intramedullary nail 100 that includes a representative image 630 of the distal bone-anchor locking hole 128. The graphical user interface can also include a representation 632 of the drill bit 616. The operator can move the drill 614 relative to the distal bone-anchor locking hole 128 until the representative images 628 and 630 of the intramedullary nail 100 and drill bit 616 are aligned. In alternative embodiments, the feedback device can provide instructions via an audio signal or lights (e.g., lighted arrows) to instruct the operator which direction(s) to move the drill 614 to align the drill bit 616 with the select locking hole.

In step 814, a bore is cut into the bone 700 with the cutting instrument 614 such that the bore extends to the select locking hole. Preferably, the bore is substantially coaxial with the select locking hole. In cutting the bore, the cutting instrument 614 can be advanced into the bone 700 a select distance. The select distance can be predetermined or can be determined during the operation. For example, the select distance can be determined based on relative positions of the cutting instrument 614 and the distal bone-anchor locking hole 128 (as determined from the position of the locator 604). Alternatively, the cutting instrument 614 can be provided with a stop or markings that can be used to determine when the cutting instrument 614 has advanced a predetermined distance.

Prior to cutting the bore, an incision can be made in the skin at the location of the select locking hole. Additionally, a guide sleeve can be inserted into the incision towards the bone 700, and the guide sleeve can receive the cutting instrument 614 as the cutting instrument cuts the bore so as to prevent the cutting instrument 614 from damaging soft tissue. After cutting the bore in the bone 700, a bone anchor 502 (FIG. 8) is inserted through the bore in step 816 and into the select locking hole so as to secure the intramedullary nail 100 to the bone 700.

In another embodiment, a method can include, after inserting the intramedullary nail 100 as described above in relation to step 802 (and optionally after inserting the proximal bone anchor in step 804), injecting or dispensing a flowable, biocompatible substance through the access hole 130 and into the cannulation 120. The flowable substance can be a viscous substance. The flowable substance can then be permitted to discharge out of the cannulation 120 and into the bone 700 through the discharge holes 132 (FIG. 5). For example, an adhesive or cement can be dispensed into the access hole 130 and caused to discharge through the discharge holes 132 so as to bond the nail body 102 to the bone. In such embodiments, at least some of the discharge holes 132 preferably extend into the outer surface 114 at a location that is spaced from the fracture site. As another example, a medicine such as an antibiotic can be dispensed into the access hole 130 and discharged through the discharge holes 132 to the fracture site in the bone so as to promote healing of the fracture. In such embodiments, at least some of the discharge holes 132 preferably extend into the outer surface 114 of the nail body 102 at a location that aligns with a fracture site. The flowable substance can be caused to discharge through the discharge holes 132 by pressurizing the flowable substance within the cannulation 120. Alternatively, the flowable substance can be caused to discharge through the discharge holes 132 through gravity or by allowing the flowable substance to take its natural path through the discharge holes 132 without pressurizing the flowable substance.

Prior to injecting or dispensing the flowable substance through the access hole 130, a bore can be formed in the bone 700 so as to provide access to the access hole 130. In particular, the aiming sleeve 400 can be received in the guide hole 228 of the aiming system 200 (assuming it is not already received or is not integral with the aiming arm 210) such that the central axis $A_S$ of the sleeve 400 is substantially aligned with both the central axis $A_G$ of the guide hole 228 and the central axis $A_B$ of the access hole 130. A cut is made in the skin of the patient (before or after receiving the sleeve 400) at a point where the central axis $A_G$ of the guide hole 228 intersects the skin, and the sleeve 400 can be advanced into the skin towards the bone 700. A cutting instrument, such as a drill bit of a drill, is then advanced through the sleeve 400 and towards the bone 700 so as to cut a bore in the bone 700 that extends to the access hole 130. Preferably, the bore in the bone has a central axis that is substantially aligned with the central axis $A_H$ of the access hole 130. The flowable substance can then be injected through the access hole 130 and into the cannulation 120.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed:

1. An intramedullary nail, comprising:
a nail body having a proximal end and a distal end that are offset from one another such that the nail body is elongate from the proximal end to the distal end, the nail body having an outer surface that extends from the proximal end to the distal end, the outer surface defining a perimeter of the intramedullary nail, the nail body having an inner surface that defines a cannulation that extends into the proximal end in a direction that extends towards the distal end, and the nail body defining:
at least one proximal bone-anchor through hole that extends into the outer surface and entirely through the intramedullary nail;
at least one distal bone-anchor through hole that extends into the outer surface and entirely through the intramedullary nail between the at least one proximal bone-anchor through hole and the distal end; and
an access hole that extends into the outer surface between the at least one proximal bone-anchor through hole and the at least one distal bone-anchor through hole, the access hole terminating at the cannulation and being in communication with the cannulation.

2. The intramedullary nail of claim 1, wherein the nail body defines a tubular wall between the inner surface and the outer surface, and the access hole extends through the tubular wall on a first side of the nail body and terminates at the tubular wall on a second side of the nail body, opposite the first side.

3. The intramedullary nail of claim 1, wherein the nail body defines a tubular wall between the inner surface and the outer surface, the access hole extends through the tubular wall on a first side of the nail body, and the access hole has a central axis that intersects the tubular wall on the second side of the nail body.

4. The intramedullary nail of claim 1, wherein the nail body has a nail-body central axis that extends from the proximal end to the distal end, the nail-body central axis extending along a first direction adjacent the access hole, and the access hole extends into the nail body along an access-hole central axis that extends along a second direction, the second direction forming an oblique angle with the first direction.

5. The intramedullary nail of claim 4, wherein the access-hole central axis is angled towards the distal end as the access hole extends from the outer surface to the inner surface.

6. The intramedullary nail of claim 1, wherein the access hole extends into the nail body along an access-hole central axis, and the access hole has a cross-sectional shape that is substantially circular in a plane that is perpendicular to the access-hole central axis.

7. The intramedullary nail of claim 1, wherein the nail body has a nail-body central axis that extends from the proximal end to the trailing end, the nail-body central axis extending along a first direction adjacent the access hole, and the access hole extends into the nail body along an access-hole central axis that extends along a second direction, the second direction forming a right angle with the first direction.

8. The intramedullary nail of claim 1, wherein the access hole extends into the nail body along an access-hole central axis, and the access hole has a cross-sectional shape that is substantially oblong in a plane that is perpendicular to the central axis of the access hole.

9. The intramedullary nail of claim 1, wherein the access hole is between all of the at least one distal bone-anchor through holes adjacent the distal end and all of the at least one proximal bone-anchor through holes adjacent the proximal end.

10. The intramedullary nail of claim 1, wherein the nail body defines a plurality of discharge holes that are configured to permit a flowable substance to discharge out of the cannulation to surrounding tissue.

11. The intramedullary nail of claim 1, wherein the intramedullary nail is devoid of bone-anchor through holes between the access hole and a midpoint of a central axis of the intramedullary nail.

12. An intramedullary nail insertion system, comprising: the intramedullary nail of claim 1; and
an aiming system comprising a handle configured to attach to the trailing end of the intramedullary nail, the aiming system comprising an aiming arm having a guide hole that has a central axis that substantially aligns with the central axis of the access hole when the aiming system is attached to the intramedullary nail.

13. An intramedullary nail insertion system, comprising: the intramedullary nail of claim 1; and
a targeting system that includes a probe having a locator and having a cable that supports the locator, the probe sized to be received through the access hole and into the cannulation so as to position the locator a location that is adjacent a select bone-anchor through hole.

14. A method of implanting an intramedullary nail into a bone, the method comprising steps of:
inserting the intramedullary nail into a medullary canal of the bone such that the intramedullary nail is elongate along the medullary canal from a proximal end of the intramedullary nail to a distal end of the intramedullary nail;
guiding a probe into a cannulation of the intramedullary nail through an access hole that extends into an outer surface of the intramedullary nail between a proximal bone-anchor through hole and a distal bone-anchor through hole;
directing the probe along the cannulation towards a select through hole of the proximal and distal bone-anchor through holes until a locator of the probe is proximate to the select through hole;
detecting a location of the select through hole based on a position of the locator;
aligning a cutting instrument with the select through hole based on the detected location;
forming a bore in the bone with the cutting instrument such that the bore extends to the select through hole; and
inserting a bone anchor through the bore and into the select through hole so as to secure the intramedullary nail to the bone.

15. The method of claim 14, wherein:
the method comprises a step of inserting, before the guiding step, a proximal bone anchor into the proximal bone-anchor through hole such that the proximal bone anchor extends through the cannulation; and
the select through hole is the distal bone-anchor through hole.

16. The method of claim 14, wherein, in the guiding step, the access hole is angled as it extends into the intramedullary nail such that a central axis of the access hole forms an oblique angle with a central axis of the intramedullary nail, and the angled access hole guides the probe into the cannulation towards the select through hole.

17. The method of claim 14, wherein the guiding step comprises guiding the probe along an aiming sleeve having a central axis that forms an oblique angle with a central axis of the intramedullary nail such that the aiming sleeve guides the probe into the cannulation towards the select through hole.

18. The method of claim 14, wherein:
the step of inserting the intramedullary nail comprises attaching a handle of an aiming system to a proximal end of the intramedullary nail and driving the intramedullary nail into the medullary canal with the handle; and
the step of guiding the probe includes guiding the probe through a guide hole in an aiming arm of the aiming system that is attached to the handle and to the access hole, wherein a central axis of the guide hole is substantially aligned with a central axis of the access hole.

19. The method of claim 14, wherein the aligning step comprises receiving instructions from a processor as to which direction to move the cutting instrument to align the cutting instrument with the select through hole, and moving the cutting instrument based on the instructions.

20. A method of promoting healing of a bone, the method comprising:
inserting an intramedullary nail into a medullary canal of the bone such that the intramedullary nail is elongate along the medullary canal from a proximal end of the intramedullary nail to a distal end of the intramedullary nail;
injecting a flowable, biocompatible substance into a cannulation of the intramedullary nail through an access hole that extends into an outer surface of the intramedullary nail between a proximal bone-anchor through hole and a distal bone-anchor through hole;
causing the flowable, biocompatible substance to discharge out of the cannulation and into the bone through at least one discharge hole that extends into the outer surface of the intramedullary nail between the proximal bone-anchor through hole and the distal bone-anchor through hole.

* * * * *